US012465665B2

(12) United States Patent
Rieck

(10) Patent No.: US 12,465,665 B2
(45) Date of Patent: Nov. 11, 2025

(54) PLASTER FOR USE IN THE CONTEXT OF AN INTRAMUSCULAR INJECTION, IN PARTICULAR A VACCINATION

(71) Applicant: PFM MEDICAL GMBH, Cologne (DE)

(72) Inventor: Monika Rieck, Cologne (DE)

(73) Assignee: PFM Medical GmbH (DE)

( * ) Notice: Subject to any disclaimer, the term of this patent is extended or adjusted under 35 U.S.C. 154(b) by 712 days.

(21) Appl. No.: 17/657,370

(22) Filed: Mar. 31, 2022

(65) Prior Publication Data

US 2023/0173134 A1 Jun. 8, 2023

(30) Foreign Application Priority Data

Apr. 8, 2021 (IT) ........................ 102021000008792

(51) Int. Cl.
*A61L 15/44* (2006.01)

(52) U.S. Cl.
CPC .................................... *A61L 15/44* (2013.01)

(58) Field of Classification Search
CPC ............ A61L 15/44; B32B 3/266; B32B 7/12
See application file for complete search history.

(56) References Cited

U.S. PATENT DOCUMENTS 5,728,071 A 3/1998 Watson et al.
6,007,562 A 12/1999 Harren et al.
7,129,389 B1 * 10/2006 Watson ............... A61F 13/0276 602/46
2018/0015050 A1 * 1/2018 Olivero ................ A61K 9/0014
2018/0153744 A1 * 6/2018 Al-Heraibi ............ A61F 13/023

FOREIGN PATENT DOCUMENTS

| | | |
|---|---|---|
| CN | 101828942 | 9/2010 |
| KR | 20020088698 | 11/2002 |
| KR | 20200040329 | 4/2020 |
| TW | M465921 | 11/2013 |

OTHER PUBLICATIONS

Immunize.org. (https://www.immunize.org/wp-content/uploads/guide/pdfs/vacc-adults-step5.pdf) Aug. 1, 2002, pp. 67-86 (Year: 2002).*
Search Report from corresponding Italian Appln. No. 102021000008792, dated Dec. 22, 2021. English translation starts on p. 3.
Office Action from related Chinese Appln. No. 202210245246.X, dated Nov. 24, 2022. English translation attached.

* cited by examiner

*Primary Examiner* — Andrew S Rosenthal
(74) *Attorney, Agent, or Firm* — Eckert Seamans Cherin & Mellott LLC

(57) ABSTRACT

The invention relates to a plaster for use in the context of an intramuscular injection, particularly a vaccination, having a patient side and an outer side, comprising: an adhesive layer on the patient side for attaching the plaster to the skin of a patient, an absorbent wound-covering on the patient side in the region of an intended intramuscular injection site, the absorbent wound-covering having received a disinfectant, and an opening on the outer side in the area of the absorbent wound-covering of the patient side for the injection needle.

18 Claims, 4 Drawing Sheets

PLASTER FOR USE IN THE CONTEXT OF AN INTRAMUSCULAR INJECTION, IN PARTICULAR A VACCINATION

FIELD

The invention relates to a plaster for use in the context of an intramuscular injection, in particular a vaccination.

BACKGROUND

In an intramuscular injection, a liquid drug is injected into a skeletal muscle. The injection is usually given into the upper arm (deltoid muscle), the thigh (vastus lateralis muscle) or the buttocks (gluteus medius or minimus muscle). To perform the intramuscular injection, the intended injection site is first disinfected. Then the liquid drug is injected into the skeletal muscle using a cannula or syringe, especially a disposable syringe. After the injection, the puncture site is covered with a swab, which in turn is fixed with an adhesive tape or plaster until the puncture site has closed.

Based on this prior art, the invention is based on the task of simplifying the performance of an intramuscular injection, in particular its preparation and post-treatment, and reducing the time required for this.

SUMMARY

The task is solved according to the invention by a plaster for use in the context of an intramuscular injection, in particular a vaccination, having a patient side and an outer side, comprising an adhesive layer on the patient side for fastening the plaster to the skin of a patient, an absorbent wound-covering on the patient side in the region of an intended puncture site of the intramuscular injection, the absorbent wound-covering having received a disinfectant, and an opening on the outer side in the region of the absorbent wound-covering of the patient side for the injection needle.

In the context of an intramuscular injection, in particular a vaccination, the plaster according to the invention is adhered to the patient's skin by means of the adhesive layer on the patient's side in preparation for the intramuscular injection. The plaster is adhered to the patient's skin in such a way that the absorbent wound-covering of the patient's side is arranged in the region of the intended injection site of the intramuscular injection. Because the absorbent dressing has absorbed a disinfectant, the intended injection site is automatically disinfected. The intramuscular injection can therefore take place through the opening of the outer side of the plaster after the plaster has been applied to the patient's skin in the area of the intended injection site. After the intramuscular injection, the injection needle is pulled out of the puncture site. As the plaster already covers the injection site, no further steps need to be taken to follow up the injection site. Rather, the plaster can simply be removed when the injection site has closed. The plaster according to the invention thus simplifies the preparation and aftercare of an intramuscular injection so that it can be performed more quickly.

The plaster according to the invention is particularly suitable for carrying out intramuscular injections, since in this case the injection needle does not have to be inserted specifically into a blood vessel, but only into a larger muscle. The exact injection site can therefore be at least partially or even completely covered by the plaster during the performance of the intramuscular injection.

In one variant according to the invention, the opening on the outer side is closed with a membrane which prevents disinfectant from escaping through the opening and enables piercing with the injection needle. This ensures that the intended injection site is disinfected by the disinfectant and that it does not escape through the opening on the outer side. At the same time, the injection needle can be pierced through the membrane. Preferably, the membrane is designed in such a way that it is not destroyed by the thin injection needle, but closes again after the injection. In particular, the membrane consists of a silicone.

According to an alternative variant of the invention, the opening on the outer side is closed with a cover which can be removed to carry out the injection. The cover is expediently designed to prevent disinfectant from escaping through the opening on the outer side. The cover of the opening on the outer side can be removed to carry out the intramuscular injection.

According to an advantageous variant, the cover is designed to close the opening on the outer side again after the injection. In this way, the opening on the outer side of the plaster can be closed again after the intramuscular injection, which prevents disinfectant or wound fluid or blood from escaping. Furthermore, the injection site is better protected from external influences.

In an expedient variant of the invention, the cover is designed as a flap which is permanently connected to the outer side of the plaster at an edge region. The flap is thus permanently connected to the outer side of the plaster and cannot be misplaced, damaged, soiled or the like during the intramuscular injection. If the flap were not permanently attached to the outer side of the plaster, it would have to be stored temporarily in a safe and clean place during the intramuscular injection.

According to one variant of the invention, the cover is at least partially self-adhesive. This allows the cover to be repeatedly attached to the outer side of the plaster, for example, to close the opening of the outer side of the plaster before and after intramuscular injection. Also, the outer surface of the plaster may comprise an additional coating or the like in the area where the cover is connected to the outer surface of the plaster, which facilitates the connection and disconnection of the cover to the outer surface of the plaster.

According to a particularly advantageous variant of the invention, the absorbent wound-covering of the patient side is arranged in the region of the opening of the outer side on the cover. The absorbent wound-covering is thus removed in the region of the opening of the outer side together with the cover in order to carry out the intramuscular injection. The injection needle is inserted directly into the patient's skin without having to penetrate the absorbent dressing. This prevents particles of the dressing from sticking to the injection needle during insertion. After the intramuscular injection, the opening is preferably closed again with the cover and the puncture site is appropriately covered by the absorbent dressing.

In a further advantageous variant of the invention, the absorbent dressing further comprises an anaesthetic and/or analgesic agent, for pre-treatment or post-treatment of the injection site of the intramuscular injection. In this way, the intramuscular injection is performed as painlessly as possible for the patient. It is also conceivable that different covers with absorbent wound-coverings are used for pre-treatment and post-treatment, each of which has absorbed different substances, for example a disinfectant and anaesthetic agent for pre-treatment and a disinfectant and analgesic agent for post-treatment. Other combinations of substances and active agents are also conceivable.

According to one variant of the invention, the adhesive layer on the patient side completely surrounds the puncture site. For example, on the patient's side, the adhesive layer is arranged completely around the edge, while the absorbent wound-covering for the intended puncture site is arranged in the middle. The intended puncture site is thus protected from external influences from all sides and no disinfectant from the absorbent wound-covering can escape over the edge area.

According to one variant of the invention, the plaster comprises a carrier layer on the patient side, which is removed before the plaster is applied to the patient's skin. Such carrier layers are known from wound plasters and protect the adhesive layer and wound-covering on the patient side before the plaster is applied to the patient's skin. Usually, this carrier layer is made in two parts, whereby first a part of the carrier layer is removed, and the plaster is applied to the patient's skin in the area of the removed carrier layer. The second, non-removed part of the carrier layer can be used for handling without touching the adhesive layer underneath. Subsequently, the second part of the carrier layer is removed, and the plaster is completely adhered to the patient's skin.

Preferably, the carrier layer is designed to be liquid-tight so that no liquid can reach the adhesive layer or the absorbent wound-covering and the disinfectant of the absorbent wound-covering cannot leak out.

In an expedient variant of the invention, the plaster has a round, oval, square, rectangular or polygonal shape.

The absorbent dressing is preferably positioned centrally on the patient side of the plaster. This allows the plaster, especially the absorbent dressing, to be placed more precisely at the intended puncture site.

According to an advantageous variant of the invention, the plaster is packaged in an outer package to protect the plaster from external influences before use. This is also known from wound plasters, for example.

Preferably, the plaster according to the invention is breathable so that the skin under the plaster can breathe. This accelerates the closure of the puncture site.

It is advisable that the wound-covering is designed in such a way that it does not adhere to the wound at the puncture site. This design is also known from wound plasters, for example.

BRIEF DESCRIPTION OF THE DRAWINGS

The invention is explained in more detail below with reference to examples of embodiments shown in the figures. They show.

DETAILED DESCRIPTION

Figure 1:
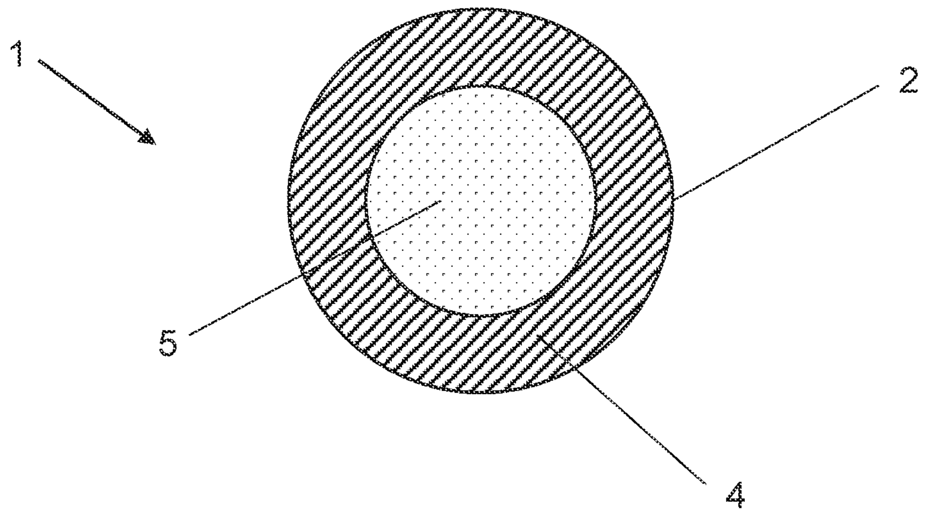
FIG. 1 a view of the patient side of a first embodiment of a plaster according to the invention, FIG. 2 a view of the outer side of the first embodiment of the plaster according to the invention of FIG. 1, FIG. 3 a view of the outer side of a second embodiment of a plaster according to the invention, FIG. 4 a view of the outer side of a third embodiment of a plaster according to the invention, FIG. 5 a detailed view of the cover from FIG. 4 from the patient side, FIG. 6 a view of the patient side of the third embodiment of the plaster according to the invention of FIG. 4, FIG. 7 a view of the outer side of a fourth embodiment of a plaster according to the invention, and FIG. 8 a detailed view of the tab from FIG. 7 from the patient's side.

FIG. 1 shows a first embodiment of a plaster 1 according to the invention for use in the context of an intramuscular injection, in particular a vaccination, with a patient side 2 and an outer side 3. FIG. 1 shows a view of the patient side 2 of the plaster 1.

The patient side 2 of the plaster 1 comprises an adhesive layer 4 for attaching the plaster 1 to the skin of a patient and an absorbent wound-covering 5 in the area of the intended injection site of the intramuscular injection. The adhesive layer 4 is designed in accordance with known wound plasters. As can be seen from FIG. 1, the adhesive layer 4 is arranged around the entire circumference of the plaster 1 and therefore completely surrounds the puncture site. The absorbent wound-covering 5 is arranged in the centre of the patient's side 2 and is enclosed by the adhesive layer 4.

In accordance with the invention, the absorbent wound-covering 5 has incorporated a disinfectant to disinfect the intramuscular injection site once the plaster 1 has been applied to the patient's skin. Suitably, the absorbent wound-covering 5 has received a liquid disinfectant.

According to one variant of the invention, the absorbent wound-covering 5 further comprises an anaesthetic and/or analgesic agent for pre-treatment or post-treatment of the injection site of the intramuscular injection. The anaesthetic and/or analgesic agent is preferably a liquid which has been absorbed by the absorbent wound-covering 5. In particular, it may be a cooling agent which has an anaesthetic and analgesic effect.

Figure 2:
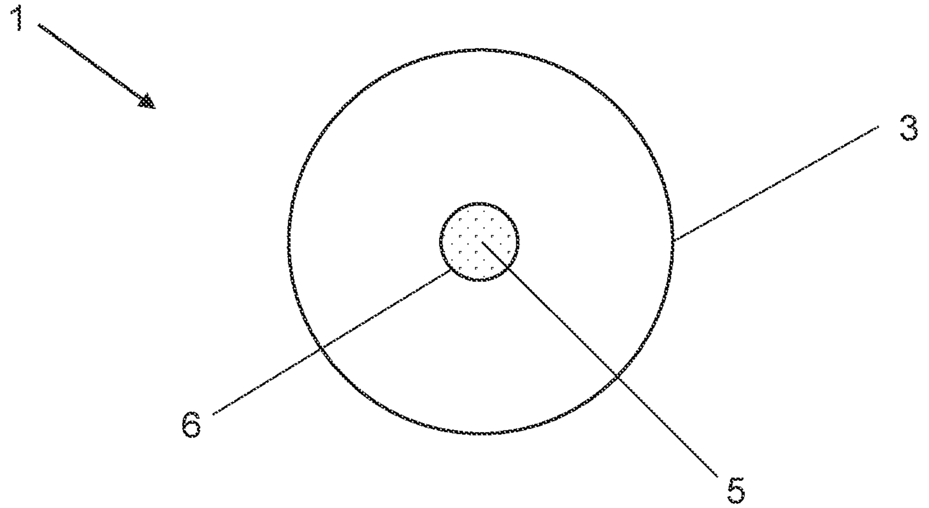

FIG. 2 shows a view of the outer side 3 of the first embodiment of the plaster 1 according to the invention of FIG. 1. The outer side 3 of the plaster 1 has an opening 6 in the region of the absorbent wound pad of the patient side 2 for the injection needle. The absorbent wound-covering 5 is visible through the opening 6. For intramuscular injection, the injection needle is inserted through the opening 6 and the absorbent wound-covering 5 into the underlying skin of the patient. For this purpose, the plaster 1 according to the invention is placed on the patient's skin in such a way that the opening 6 is located in the region of the intended injection site, in particular in the region of the upper arm (deltoid muscle), the thigh (vastus lateralis muscle) or the buttocks (gluteus medius or minimus muscle).

Figure 3:
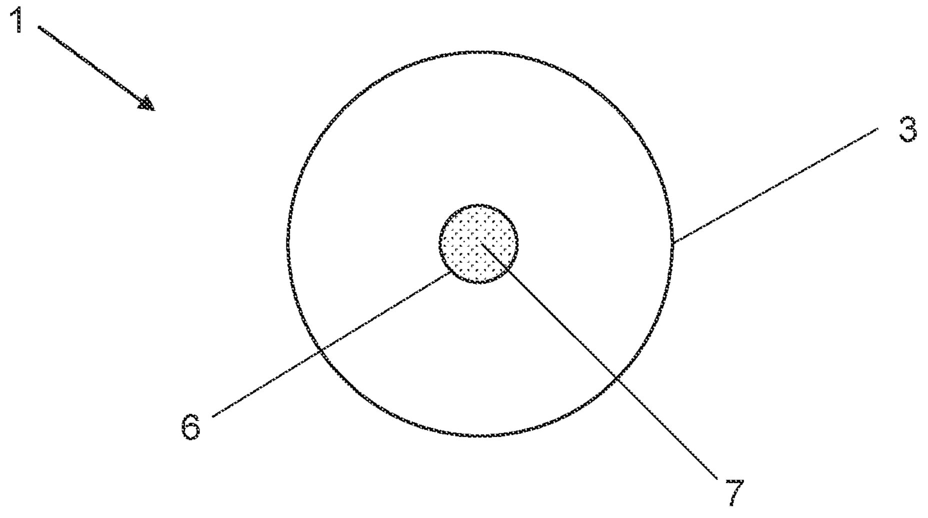

FIG. 3 shows a view of an outer side 3 of a second embodiment of a plaster 1 according to the invention. The second embodiment of FIG. 3 differs from the first embodiment of FIGS. 1 and 2 in that the opening 6 on the outer side 3 is closed with a membrane 7. The membrane 7 prevents disinfectant from escaping through the opening 6 and at the same time enables piercing with the injection needle. Due to the membrane 7, the absorbent wound-covering 5 is not visible from the outer side 3, unless the membrane 7 is transparent.

The patient side 2 of the second embodiment in FIG. 3 is, for example, identical to the patient side 2 of the first embodiment as shown in FIG. 1.

Figure 4:
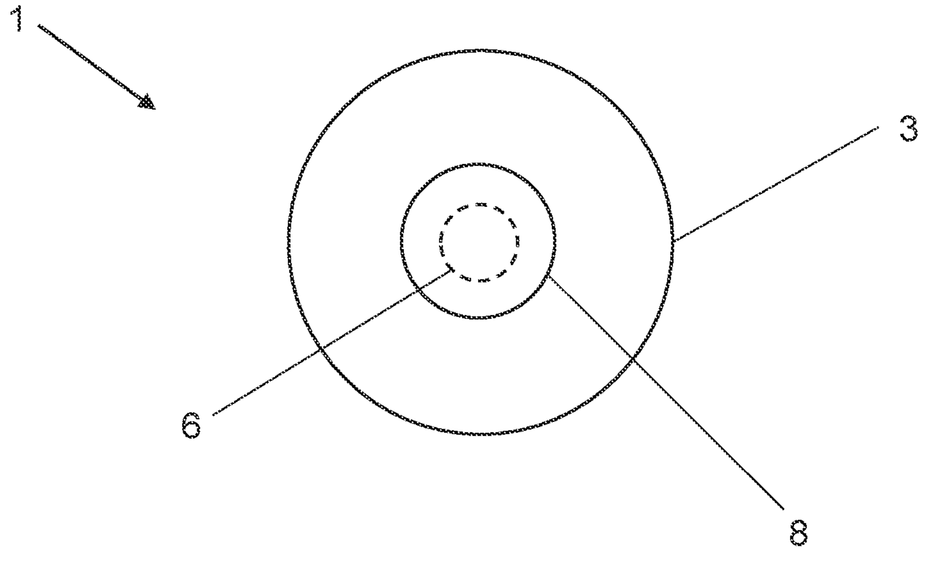

FIG. 4 shows a view of an outer side 3 of a third embodiment of a plaster 1 according to the invention. According to the third embodiment, the opening 6 on the outer side 3 is closed with a cover 8. The cover 8 can be removed for carrying out the intramuscular injection. Expediently, the cover 8 is designed to close the opening 6 again after the injection. For this purpose, the cover 8 is at least partially self-adhesive, in particular in the area where the cover 8 is attached to the outer side 3 of the plaster 1.

Figure 5:
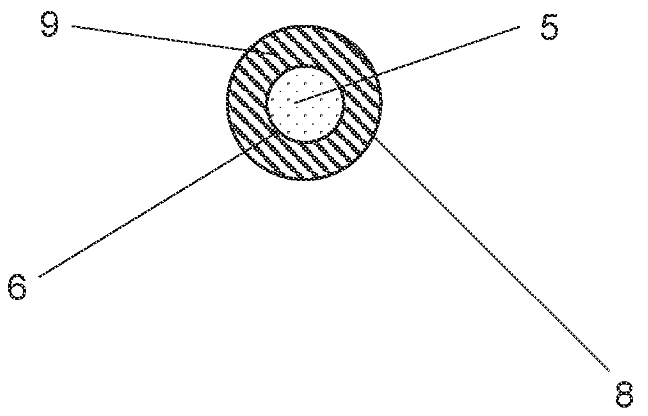

FIG. 5 shows a detailed view of the cover 8 from the patient side 2, i.e. the side of the cover 8 that is attached to the outer side 3 of the plaster 1 to close the opening 6. In the area where the cover 8 rests on the outer side 3 of the plaster 1, the cover 8 has an adhesive layer 9. In the area of the opening 6 of the outer side 3 of the plaster 1, the absorbent wound-covering 5 is preferably attached to the cover 8, i.e. within the adhesive layer 9. This has the advantage that the absorbent wound-covering 5 is removed with the cover in order to perform the intramuscular injection and the puncture site is visible.

Figure 6:
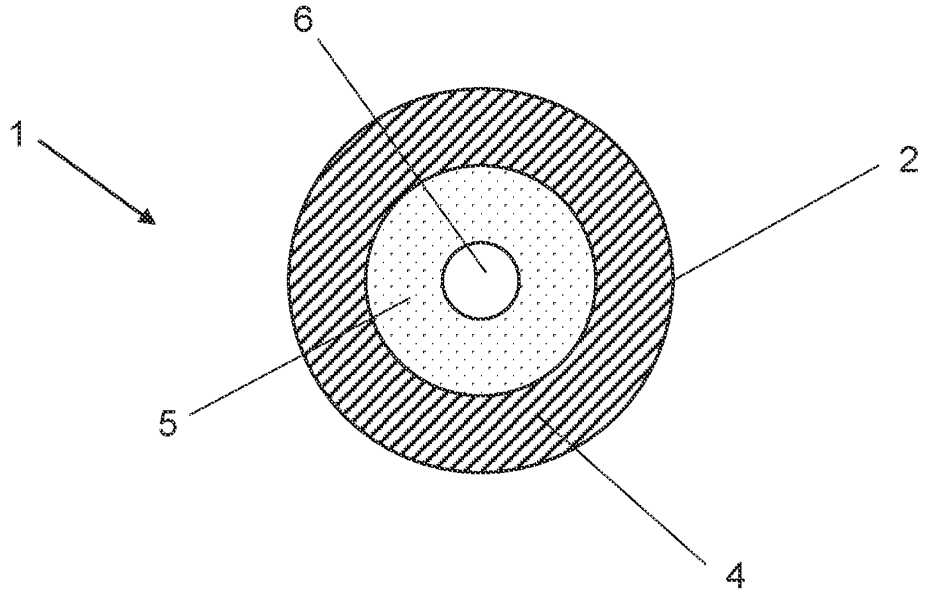

FIG. 6 shows a view of the patient side 2 of the third embodiment of the plaster 1 according to the invention of FIG. 4. It can be seen from FIG. 6 that in the region of the opening 6 the absorbent wound pad 5 is arranged on the cover 8 and completely exposes the opening when the cover 8 is removed, as shown in FIG. 6. Outside the opening 6, but in the area around the opening 6, the patient side 2 of the plaster 1 has further absorbent wound-covering 5.

Figure 7:
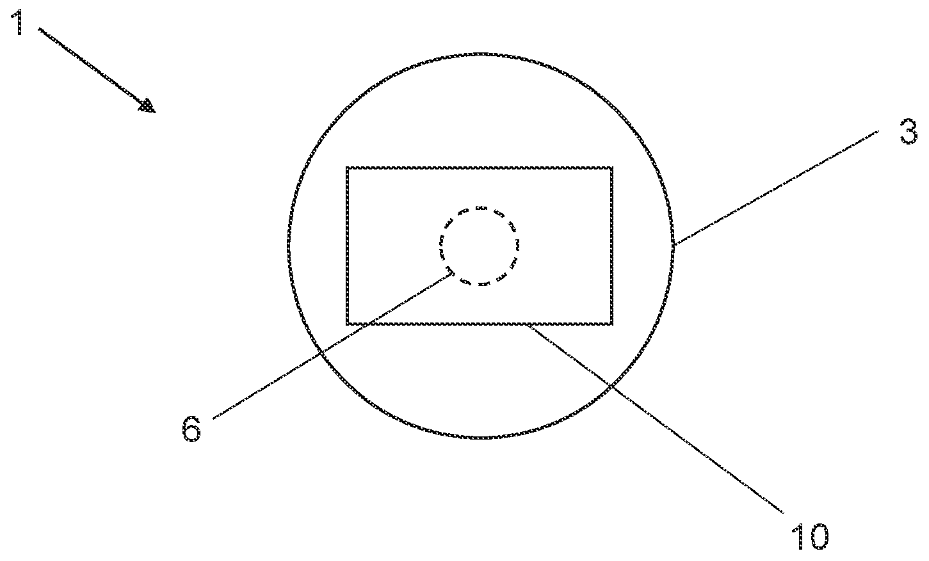

FIG. 7 shows a view of the outer side 3 of a fourth embodiment of a plaster 1 according to the invention. The fourth embodiment of FIG. 7 differs from the third embodiment of FIGS. 4 to 6 in that the cover 8 is designed as a flap 10 which is permanently connected to the outer side 3 of the plaster 1 at an edge region. The flap 10 can be unfolded to carry out the intramuscular injection in order to expose the injection site, but at the same time remains permanently connected to the outer side 3 of the plaster 1. The permanent connection can be made, for example, by a stronger adhesive, welding, sewing or other connection method.

Figure 8:
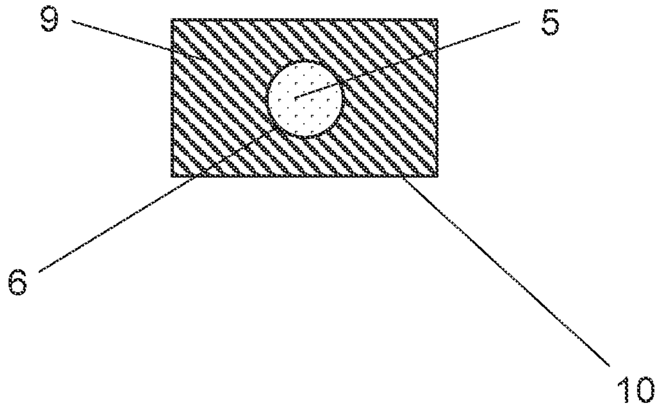

FIG. 8 shows a detailed view of the flap 10 of FIG. 7 from the patient side 2, i.e. the side connected to the outer side 3 of the plaster 1. As described with regard to the third embodiment from FIGS. 4 to 6, the flap 10 also preferably comprises the absorbent wound pad 5 in the region of the opening 6 of the plaster 1. The surface of the flap 10 facing the outer side 3 of the plaster 1 comprises an adhesive layer 9 in order to be able to repeatedly close the opening 6 of the plaster 1. In one variant, the flap 10 can also comprise a section in an edge region in which no adhesive 9 is arranged, which improves the manageability, in particular making it easier to detach the flap 10 from the outer side 3 of the plaster 1.

Even though the flap 10 is shown separately in FIG. 8, it is permanently connected to the outer side 3 of the plaster 1 on at least one edge area.

The patient side 2 of the fourth embodiment of the plaster 1 according to the invention corresponds, for example, to the patient side 2 of the third embodiment of the plaster 1 according to the invention as shown in FIG. 6.

LIST OF REFERENCE SIGNS

1 Plaster
2 Patient side
3 Outer side
4 Adhesive layer (plaster)
5 absorbent dressing
6 Opening for injection needle
7 Membrane
8 Cover
9 Adhesive layer (cover/tab)
10 flap

What is claimed is:

1. A plaster for use in the context of an intramuscular injection having a patient side and an outer side, comprising:
- an adhesive layer on the patient side for attaching the plaster to the skin of a patient;
- an absorbent wound-covering arranged in the center of the adhesive layer on the patient side in the region of an intended intramuscular injection site, the absorbent wound-covering having received a disinfectant; and
- an opening in the adhesive layer on the outer side in the area of the absorbent wound-covering of the patient side sized for the intramuscular injection,
- wherein the plaster totally covers the intended injection site and the absorbent wound-covering is visible through the opening,
- wherein a diameter of the absorbent wound-covering is less than a diameter of the adhesive layer such that the adhesive layer extends beyond an outer perimeter of the absorbent wound-covering, and
- wherein a diameter of the opening on the outer side is smaller than the diameter of the absorbent wound-covering on the patient side.

2. The plaster according to claim 1, wherein the opening on the outer side is closed with a membrane which prevents the disinfectant from escaping through the opening and allows piercing with an injection needle.

3. The plaster according to claim 1, wherein the opening on the outer side is closed with a cover which can be removed for carrying out the injection.

4. The plaster according to claim 3, wherein the cover is designed to close the opening on the outer side again after the injection.

5. The plaster according to claim 4, wherein the cover is formed as a flap which is permanently connected to the outer side of the plaster at an edge region.

6. The plaster according to claim 3, wherein the cover is at least partially self-adhesive.

7. The plaster according to claim 1, wherein the absorbent wound-covering further comprises an anaesthetic agent, an analgesic agent, or both for pre-treatment or post-treatment of the injection site of the intramuscular injection.

8. The plaster according to claim 1, wherein the plaster comprises a carrier layer on the patient side, which carrier layer is removed before the plaster is applied to the patient's skin.

9. A plaster for use in the context of an intramuscular injection having a patient side and an outer side, the plaster comprising:
- an adhesive layer on the patient side for attaching the plaster to the skin of a patient;
- an absorbent wound-covering arranged in the center of the adhesive layer on the patient side in the region of an intended intramuscular injection site, the absorbent wound-covering having received a disinfectant;
- an opening in the adhesive layer on the outer side in the area of the absorbent wound-covering of the patient side for the intramuscular injection, and
- a membrane arranged on and closing the opening on the outer side, wherein the membrane prevents the disinfectant from escaping through the opening and allows piercing with an injection needle,
- wherein the plaster totally covers the intended injection site and the absorbent wound-covering is visible through the membrane covering the opening, and
- wherein a diameter of the absorbent wound-covering is less than a diameter of the adhesive layer such that the adhesive layer extends beyond an outer perimeter of the absorbent wound-covering.

10. The plaster according to claim 9, wherein a diameter of the opening on the outer side is smaller than the diameter of the absorbent wound-covering on the patient side.

11. The plaster according to claim 9, wherein the absorbent wound-covering further comprises an anaesthetic agent, an analgesic agent, or both for pre-treatment or post-treatment of the injection site of the intramuscular injection.

12. The plaster according to claim 9, wherein the adhesive layer on the patient side completely surrounds the intended injection site.

13. The plaster according to claim 9, wherein the plaster comprises a carrier layer on the patient side, which carrier layer is removed before the plaster is applied to the patient's skin.

14. A plaster for use in the context of an intramuscular injection having a patient side and an outer side, comprising:

an adhesive layer on the patient side for attaching the plaster to the skin of a patient;

an absorbent wound-covering arranged in the center of the adhesive layer on the patient side in the region of an intended intramuscular injection site, the absorbent wound-covering having received a disinfectant; and an opening on the outer side in the area of the absorbent wound-covering of the patient side for the intramuscular injection, wherein the plaster totally covers the intended injection site and the absorbent wound-covering is visible through the opening, and wherein the opening on the outer side is closed with a cover which can be removed for carrying out the injection.

15. The plaster according to claim 14, wherein the cover is designed to close the opening on the outer side again after the injection.

16. The plaster according to claim 15, wherein the cover is formed as a flap which is permanently connected to the outer side of the plaster at an edge region, wherein the cover is at least partially self-adhesive.

17. The plaster according to claim 14, wherein the absorbent wound-covering further comprises an anaesthetic and/or analgesic agent for pre-treatment or post-treatment of the injection site of the intramuscular injection.

18. The plaster according to claim 14, wherein the adhesive layer on the patient side completely surrounds the intended injection site.

* * * * *